United States Patent [19]

Arakelian et al.

[11] 4,246,126
[45] Jan. 20, 1981

[54] 2,5-DIMERCAPTO-1,3,4-THIADIAZOLE DERIVATIVES AND LUBRICANTS CONTAINING THEM

[75] Inventors: Arthur N. Arakelian, Cleveland; Kirk E. Davis, Euclid, both of Ohio

[73] Assignee: The Lubrizol Corporation, Wickliffe, Ohio

[21] Appl. No.: 43,071

[22] Filed: May 29, 1979

[51] Int. Cl.$^3$ .............................................. C10M 1/38
[52] U.S. Cl. .................................... 252/47.5; 548/142
[58] Field of Search ......................... 252/47.5; 548/142

[56] References Cited

U.S. PATENT DOCUMENTS

| | | | |
|---|---|---|---|
| 2,703,785 | 3/1955 | Roberts et al. | 548/142 X |
| 2,749,311 | 6/1956 | Sabol et al. | 548/142 X |
| 2,799,652 | 7/1957 | Fields | 252/47.5 X |
| 3,087,932 | 4/1963 | Little, Jr. | 548/142 |
| 3,663,561 | 5/1972 | Blaha | 548/142 |
| 4,097,387 | 6/1978 | Caspari | 252/47.5 |
| 4,140,643 | 2/1979 | Davis | 252/47.5 |

*Primary Examiner*—Andrew Metz
*Attorney, Agent, or Firm*—Daniel N. Hall; William H. Pittman; Raymond F. Keller

[57] ABSTRACT

A novel nitrogen and sulfur composition is prepared by the reaction of 2,5-dimercapto-1,3,4-thiadiazole with a peroxide, preferably hydrogen peroxide. This nitrogen and sulfur composition may be reacted with polysulfides, mercaptans and amino compounds (especially oil-soluble, nitrogen-containing dispersants) to produce lubricant additives having decreased copper activity and a decreased tendency for "lead paint" deposition.

14 Claims, No Drawings

2,5-DIMERCAPTO-1,3,4-THIADIAZOLE DERIVATIVES AND LUBRICANTS CONTAINING THEM

This invention relates to a new composition of matter, a method for preparing it, and methods for using it in the production of other useful compositions. In a particular sense, the composition principally contemplated according to this invention is a nitrogen and sulfur composition prepared by the reaction of at least one peroxy compound with 2,5-dimercapto-1,3,4-thiadiazole.

It is well known that various derivatives of 2,5-dimercapto-1,3,4-thiadiazole (hereinafter sometimes referred to as DMTD) are useful lubricant additives for the inhibition of copper activity (corrosion or staining) and "lead paint" deposition. Many patents have issued on additives containing DMTD nuclei. Because of the insolubility of DMTD itself in mineral oils of the type useful as lubricant bases, further reaction of some kind or another is necessary in order to produce oil-dispersible products. It is of interest to maximize the amount of DMTD or similar moieties in these oil-soluble materials, so as to obtain optimum effect thereof when the materials are incorporated in lubricants.

A principal object of this invention, therefore, is to provide novel chemical compositions and method for their production.

A further object is to provide compositions convenient for the incorporation of DMTD or similar moieties into oil-soluble or oil-dispersible compositions.

Still another object is to provide a method for the preparation of compositions containing relatively large amounts of DMTD moieties, for use in suppressing copper activity and "lead paint" depositions in lubricants.

Other objects will in part be obvious and will in part appear hereinafter.

As previously noted, the nitrogen and sulfur compositions principally contemplated by this invention are prepared by reacting at least one peroxy compound with DMTD. Suitable peroxy compounds include hydrogen peroxide, sodium peroxide, and various organic peroxy compounds such as benzoyl peroxide and t-butyl peroxide. Because of its availability and relatively low cost, hydrogen peroxide is often preferred. It may be conveniently used in 30% aqueous solution, although more dilute solutions may be used if desired.

Ordinarily, at least about one mole of peroxide is used per mole of DMTD to produce the compositions of this invention. Frequently a slight excess of peroxide, typically up to about 1.5 mole and usually up to about 1.2 mole per mole of DMTD, is employed. Reaction temperatures from room temperature to about 75° C. are normally adequate for the preparation of the nitrogen and sulfur compositions of this invention. The reaction is conveniently effected by adding the peroxide to a DMTD solution or suspension in water, an alcohol or the like. The product precipitates therefrom and may be easily isolated by filtration.

The preparation of the nitrogen and sulfur compositions of this invention is illustrated by the following examples. All parts and percentages are by weight.

EXAMPLE 1

To a suspension of 1500 parts by weight (10 moles) of DMTD in 7500 parts of water is added over 6½ hours, with stirring, 1247 parts (11 moles) of 30% hydrogen peroxide. An exothermic reaction takes place which causes a temperature increase to 48° C. After stirring for an additional 5 hours, the solid material which precipitates is filtered, washed with water and dried in a steam oven. This solid is the desired product which contains 65.8% sulfur and 18.03% nitrogen. It has acid numbers of 702 to phenolphthalein and 5.0 to bromphenol blue.

EXAMPLE 2

Following the procedure of Example 1, a product is made from 1740 parts (10 moles) of DMTD containing 13% water, 7500 parts of water and 1130 parts (10 moles) of 30% hydrogen peroxide. The solid product, after drying for 7 days at room temperature, has acid numbers of 554 to phenolphthalein and 17.9 to bromphenol blue.

The nitrogen and sulfur composition prepared as described hereinabove is insoluble in water and in most organic solvents. It is also insoluble in mineral oil. However, it reacts with many oil-dispersible materials to produce oil-soluble or oil-dispersible products characterized by low copper activity and "lead paint" deposition. Among the compositions with which these nitrogen and sulfur compositions will react are those containing polysulfide groups, mercapto groups and amino >N—H groups. The resulting products are sometimes referred to hereinafter as "adducts". They have chemical properties which, from the standpoint of utility as lubricant additives, are similar to those of the reaction products of the corresponding compounds with DMTD and its salts. In some instances the adducts of this invention have properties superior to those of the corresponding DMTD products; for example, the adducts with carboxylic dispersants (as defined hereinafter) are frequently less corrosive to lead than the reaction products of the dispersants with DMTD.

The reaction of the nitrogen and sulfur composition with polysulfides is of particular significance because of the tendency of polysulfides to have high sulfur activity. The preparation of an adduct serves to substantially decrease such activity.

Among the polysulfide adducts which may be prepared are those with sulfurized olefins such as described in U.S. Pat. No. 4,119,549 and 4,119,550; with sulfurized ester-olefin or ester-olefin-fatty acid compositions such as described in U.S. Pat. No. 3,953,347 and 4,053,427; with sulfurized alicyclic olefinic compounds such as described in U.S. Pat. No. Re. 27,331; and with sulfurized aromatic compounds such as those described in a large number of United States patents including U.S. Pat. Nos. 2,198,828; 2,263,445; and 3,285,854. All of the above-identified patents are incorporated by reference herein for their disclosures of such polysulfides. The sulfurization products of olefinic compounds, especially aliphatic olefins and most desirably those containing from about 6 to about 20 carbon atoms, are preferred as precursors for the adducts of this invention.

Mercaptan adducts may be made from various aliphatic mercapto compounds such as the octyl, nonyl, decyl, dodecyl, tetradecyl and eicosyl mercaptans and from aromatic mercapto compounds such as thiophenol and the thionaphthols. Adducts with the aliphatic mercaptans are preferred, especially those containing at least about 10 carbon atoms.

Adducts may also be prepared with amino compounds containing at least one hydrogen atom bonded to a nitrogen atom; that is, with compounds containing at least one primary or secondary amino group. Suitable materials include aliphatic amines, aromatic amines, heterocyclic amines, and oil-soluble dispersants containing such amino groups. A large variety of suitable dispersants is disclosed in U.S. Pat. No. 4,136,043 (which further discloses products obtained by heating such dispersants with dimercaptothiadiazoles such as DMTD) which is incorporated by reference herein for such disclosure. These dispersants include "carboxylic dispersants" which are reaction products of various relatively high molecular weight carboxylic acids or derivatives thereof with nitrogen-containing compounds; "amine dispersants" which are the reaction products of amines with aliphatic or alicyclic halides; and "Mannich dispersants" which are reaction products of alkyl phenols with aldehydes (especially formaldehyde) and amines.

Among the dispersants useful for adduct preparation are the carboxylic dispersants characterized by the presence within their molecular structure of at least one acyl, acyloxy or acylimidoyl radical containing at least about 30 carbon atoms and at least one radical in which a nitrogen or oxygen atom is attached directly to said acyl, acyloxy or acylimidoyl radical, said nitrogen or oxygen atom also being attached to a hydrocarbon or substituted hydrocarbon radical. Preferred dispersants of this type may be prepared by the reaction of a substantially saturated succinic acid, anhydride, acid halide, ester, amide, imide or amidine containing a hydrocarbon or substituted hydrocarbon radical with at least one of an alcohol and an alkylene polyamine. Especially desirable are the mixed oxygen- and nitrogen-bridged dispersants prepared by sequentially reacting a succinic acid, anhydride, acid halide, ester, amide, imide or amidine having a hydrocarbon substituent which contains at least about 50 carbon atoms with at least one alcohol and at least one alkylene polyamine.

Another class of dispersants from which adducts may be prepared are alkylated aminophenols. Descriptions of these materials appear in copending application Ser. No. 714,207, filed Aug. 13, 1976, and in German application (OS) No. 2,736,360; and also in copending application Ser. No. 676,172, filed Apr. 12, 1976, and German application (OS) No. 2,646,241. These applications are incorporated by reference herein for their disclosure of suitable alkylated aminophenol dispersants.

The adducts of this invention are generally prepared by merely heating the desired reactant with the nitrogen and sulfur composition, typically at temperatures between about 100° and about 200° C. If desired, a substantially inert, normally liquid organic diluent such as xylene or mineral oil may be used as a reaction medium. The proportions of ingredients are not critical so long as the amount of nitrogen and sulfur composition used is not so great as to cause insolubility of a substantial amount of the product in the medium (e.g., mineral oil) in which it is to be used. Generally, the amount of nitrogen and sulfur composition used is the minimum required to cause the desired reduction in copper activity and "lead paint" deposition. The required amount of nitrogen and sulfur composition may be as low as about 1 part by weight and as high as about 80 parts per 100 parts of polysulfide, mercaptan or amino composition. In general, higher ratios of nitrogen and sulfur composition are required when the other reagent is a mercaptan than when it is a polysulfide or dispersant. For example, a typical mercaptan adduct may contain as much as between about 20 and about 80 parts of nitrogen and sulfur composition per 100 parts of mercaptan, while a polysulfide or dispersant adduct may often contain as little as between about 1 and about 10 parts of nitrogen and sulfur composition per 100 parts of polysulfide or dispersant.

The preparation of the adducts of this invention is illustrated by the following examples. All parts are by weight.

EXAMPLE 3 n-Dodecyl disulfide, 20.1 parts, is heated to 90° C. with stirring and 7.4 parts of the product of Example 2 is added portionwise over 1½ hours. The temperature is gradually increased to 150° C. during the addition and for an additional one-half hour thereafter. The mixture is then cooled to 50° C. and filtered, using a filter aid material. The product is the desired adduct having an acid number to phenolphthalein of 23.

EXAMPLE 4

A polysulfide is prepared by the reaction of 2 moles of diisobutene with 3 moles of sulfur and 1 mole of hydrogen sulfide at about 100° C., followed by vacuum stripping and filtration. To 400 parts of this product is added 8 parts of the product of Example 1. The mixture is heated to 135° C. for 3½ hours and is then filtered, using a filter aid material, to yield the desired adduct.

EXAMPLE 5

To 400 parts of the polysulfide of Example 4 is added 12 parts of the product of Example 1. The mixture is heated to 130°–135° for about 3½ hours, cooled to room temperature and filtered using a filter aid material. The product is the desired adduct.

EXAMPLE 6

A mixture of 51 parts of t-dodecyl mercaptan, 37 parts of the product of Example 2 and 88 parts of xylene is heated under reflux, with stirring, for 2 hours, cooled to room temperature and filtered using a filter aid material. The filtrate is the desired adduct (50% solution in xylene) containing 4.41% nitrogen and 18.41% sulfur.

EXAMPLE 7

A mixture of 1900 parts of the dispersant of Example 11 of U.S. Pat. No. 4,136,043 (said dispersant containing about 43% mineral oil) and 100 parts of the product of Example 2 is heated to 140°–150° C. under nitrogen, with stirring, until a clear liquid is formed. Mineral oil, 290 parts, is added and the solution is filtered at 130°–140° C., using a filter aid material. The filtrate is the desired adduct in mineral oil solution; it contains 1.06% nitrogen and 2.56% sulfur.

EXAMPLE 8

A mixture of 125 parts of an alkylated aminophenol dispersant (in mineral oil solution) prepared according to Examples 4 and 5 of the aforementioned application Ser. No. 714,207 and German application No. 2,736,360, and about 0.4 parts of the product of Example 1 is heated to 125° C., with stirring. Additional increments of the product of Example 1, to a total of 8.3 parts, are added over about 5 minutes at 125°–135° C. The mixture is stirred at 135° C. for ½ hour and finally to 140° C., whereupon it is filtered with the addition of a filter aid material. The filtrate is the desired product and contains 2.49% sulfur.

The adducts of this invention are useful as additives for lubricants, in which they function in the same way as their precursors but in addition have reduced copper activity and tendency to deposit "lead paint". They can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic transmission fluids, transaxle lubricants, gear lubricants, metal-working lubricants, hydraulic fluids and other lubricating oil and grease compositions can also benefit from the incorporation therein of the compositions of the present invention.

Natural oils include animal oils and vegetable oils (e.g., castor oil, lard oil) as well as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins [e.g., polybutylenes, polypropylenes, propylene-isobutylene copolymers, chlorinated polybutylenes, poly(1-hexenes), poly(1-octenes), poly(1-decenes), etc. and mixtures thereof]; alkylbenzenes (e.g., dodecylbenzenes, tetradecylbenzenes, dinonylbenzenes, di(2-ethylhexyl)benzenes, etc.); polyphenyls (e.g., biphenyls, terphenyls, alkylated polyphenyls, etc.), alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic lubricating oils. These are exemplified by the oils prepared through polymerization of ethylene oxide or propylene oxide, the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such neopentyl glycol, trimethylolpropane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl) silicate, tetra-(4-methyl-2-ethylhexyl) silicate, tetra-(p-tert-butylphenyl) silicate, hexa-(4-methyl-2-pentoxy)-disiloxane, poly(methyl)-siloxanes, poly(methylphenyl)siloxanes, etc.). Other synthetic lubricating oils include liquid esters of phosphorus-containing acids (e.g., tricresyl phosphate, trioctyl phosphate, diethyl ester of decylphosphonic acid, etc.), polymeric tetrahydrofurans and the like.

Unrefined, refined and rerefined oils (and mixtures of each with each other) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Generally, the lubricants of the present invention contain an amount of the adduct of this invention sufficient to provide it with the desired properties. Normally this amount will be from about 0.1 to about 20 parts, preferably from about 1.0 to about 10 parts, per 100 parts of lubricant.

The invention also contemplates the use of other additives in combination with the adducts of this invention. Such additives may include detergents and dispersants of the ash-producing or ashless type, corrosion- and oxidation-inhibiting agents, pour point depressing agents, extreme pressure agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-$\beta$-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°-200° C.

The ashless detergents and dispersants are exemplified by those described in the aforementioned U.S. and German patents and applications.

Extreme pressure agents and corrosion- and oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

The adducts of this invention can be added directly to the lubricant. Preferably, however, they are diluted with a substantially inert, normally liquid organic diluent such as mineral oil, naphtha, benzene, toluene or xylene, to form an additive concentrate. These concentrates usually contain from about 20% to about 90% by weight of the adduct of this invention and may contain, in addition, one or more other additives known in the art or described hereinabove.

What is claimed is:

1. A method for preparing a nitrogen- and sulfur-containing composition which comprises reacting, at a temperature from room temperature to about 75° C., at least one peroxy compound with 2,5-dimercapto-1,3,4-thiadiazole; about 1–1.5 mole of peroxy compound being employed per mole of 2,5-dimercapto-1,3,4-thiadiazole.

2. A method according to claim 1 wherein the peroxy compound is hydrogen peroxide.

3. A nitrogen and sulfur composition prepared by the method of claim 1 or 2.

4. A method for preparing a nitrogen- and sulfur-containing adduct which comprises reacting, at a temperature between about 100° and about 200° C., about 1–80 parts by weight of the composition of claim 1 with 100 parts of at least one organic polysulfide.

5. A method according to claim 4 wherein the polysulfide is prepared by sulfurizing at least one aliphatic olefin containing from about 6 to about 20 carbon atoms.

6. A method for preparing a nitrogen- and sulfur-containing adduct which comprises reacting, at a temperature between about 100° and about 200° C., about 1–80 parts by weight of the composition of claim 1 with 100 parts of at least one organic compound containing a primary or secondary amine group selected from the group consisting of aliphatic amines, aromatic amines, heterocyclic amines and oil-soluble nitrogen-containing dispersants.

7. A method according to claim 6 wherein the organic compound is an oil-soluble nitrogen-containing dispersant.

8. A method according to claim 7 wherein the dispersant is a carboxylic dispersant characterized by the presence within its molecular structure of at least one acyl, acyloxy or acylimidoyl radical containing at least about 30 carbon atoms and at least one radical in which a nitrogen or oxygen atom is attached directly to said acyl, acyloxy or acylimidoyl radical, said nitrogen or oxygen atom also being attached to a hydrocarbon or substituted hydrocarbon radical.

9. A method according to claim 8 wherein the dispersant is prepared by the reaction of a substantially saturated succinic acid, anhydride, acid halide, ester, amide, imide or amidine containing a hydrocarbon or substituted hydrocarbon radical with at least one of an alcohol and an alkylene polyamine.

10. A method according to claim 9 wherein the dispersant is a mixed oxygen- and nitrogen-bridged dispersant prepared by sequentially reacting a succinic acid, anhydride, acid halide, ester, amide, imide or amidine having a hydrocarbon substituent which contains at least about 50 carbon atoms with at least one alcohol and at least one alkylene polyamine.

11. A method according to claim 10 wherein the hydrocarbon substituent is derived from an isobutene polymer.

12. A nitrogen- and sulfur-containing adduct prepared by the method of any of claims 4 and 6–11.

13. An additive concentrate comprising a substantially inert, normally liquid organic diluent and from about 20% to about 90% by weight of an adduct according to claim 12.

14. A lubricant comprising a major amount of a lubricating oil and from about 0.1 to about 20 parts by weight, per 100 parts of said lubricant, of an adduct according to claim 12.

* * * * *